United States Patent
Diehl et al.

(10) Patent No.: US 8,120,359 B2
(45) Date of Patent: Feb. 21, 2012

(54) MAGNETIC RESONANCE APPARATUS AND METHOD FOR DETERMINING A PULSE SEQUENCE TO FEED AN RF RADIATING COIL

(75) Inventors: Dirk Diehl, Erlangen (DE); Rene Gumbrecht, Herzogenaurach (DE); Juergen Nistler, Erlangen (DE); Wolfgang Renz, Erlangen (DE); Markus Vester, Nuremberg (DE); Sebastian Wolf, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 184 days.

(21) Appl. No.: 12/487,748

(22) Filed: Jun. 19, 2009

(65) Prior Publication Data
US 2009/0322329 A1    Dec. 31, 2009

(30) Foreign Application Priority Data
Jun. 19, 2008   (DE) .......................... 10 2008 029 175

(51) Int. Cl.
*G01V 3/00*    (2006.01)

(52) U.S. Cl. ....................................................... 324/309

(58) Field of Classification Search .......... 324/300–322; 600/410–435; 702/19, 85–107, 189–199; 382/128–134
See application file for complete search history.

(56) References Cited

U.S. PATENT DOCUMENTS

| | | | |
|---|---|---|---|
| 4,709,212 A * | 11/1987 | MacFall et al. | 324/309 |
| 6,291,996 B1 * | 9/2001 | Glover et al. | 324/309 |
| 7,786,729 B2 * | 8/2010 | Chamberlain et al. | 324/309 |
| 7,800,368 B2 * | 9/2010 | Vaughan et al. | 324/318 |

* cited by examiner

*Primary Examiner* — Dixomara Vargas
(74) *Attorney, Agent, or Firm* — Schiff Hardin LLP

(57) ABSTRACT

In a magnetic resonance apparatus having an RF radiating coil and gradient coils, and in a method for operating such a magnetic resonance apparatus, a pulse sequence, composed of multiple time steps, is specified for operating the gradient coils to time-dependently select regions of a selected slice of a selected volume of a subject. A non-linear equation system is then solved to obtain feed parameters for individual channels of the transmit coil for each time step, with specification of a desired target magnetization, and dependent on the pulse sequence specified for the gradient coils. The non-linear equation system is based on discrete values for time and space variable and, in addition to equations resulting from the Bloch equation, which are non-linear in their feed parameters, includes at least one additional equation that describes boundary conditions for the examination of the subject.

18 Claims, 4 Drawing Sheets

MAGNETIC RESONANCE APPARATUS AND METHOD FOR DETERMINING A PULSE SEQUENCE TO FEED AN RF RADIATING COIL

BACKGROUND OF THE INVENTION

1. Field of the Invention

The present invention relates to a method for determining a pulse sequence for feeding a radio-frequency transmit coil having one transmit channel, or a number of transmit channels, in a magnetic resonance apparatus.

2. Description of the Prior Art

For feeding the radio-frequency transmit coils in order to produce a deflection of the spin from the equilibrium magnetization, conventional magnetic resonance (MR) apparatuses use parameters that are designed such that the produced deflection field (often also called the B1 field) is as homogenous as possible within the measurement region not occupied by a person. It is to be noted at the outset that the designation "radio-frequency transmit coil" also encompasses transmit and receive coils throughout.

Particularly in newer MR apparatuses, for example equipment having a base magnetic field strength greater than or equal to 3 tesla, it has however turned out that this homogeneity can be disrupted already by the introduction of a patient, because eddy currents are produced in the patient that in turn produce interference fields that destroy the homogeneity of the deflection field, and thus of the magnetization. This increase in the eddy current effect is due to the obligatory use of higher frequencies.

In the aforementioned, long-known cases, the feeding conventionally takes place in such a way that given n excitation channels of the coil, the successive channels are fed so as to be respectively offset by 2π/n, in order to achieve a circularly polarized field. This manner of operation produces a homogenous deflection field in empty space, and is often referred to as "mode 1."

A first approach to solving the aforementioned problems is called the static approach. Here, the phase and amplitude are held constant for each channel for the entire duration of the excitation in order to achieve a more homogenous magnetization. However, the improvements achieved thereby are not adequate, and enable neither an optimization with respect to the SAR exposure of the patient nor as is frequently desirable, a solely local deflection of the spin.

In order to solve the last-noted problem, it has been proposed to use the gradient coils, which during the excitation are normally inactive except for the slice selection gradient, during the radio-frequency excitation pulse as well, in order to select particular regions of the slice to be excited in a time-resolved manner. In parallel, it has been proposed to permit a dynamic change in the phase and amplitude of the transmit channels during the duration of the excitation, so that a pulse sequence results. A particular region is then, so to speak, selected and correspondingly excited, and in the next time step a different region is processed. For this purpose, a k-space trajectory for the gradient coils is specified that selects the partial volumes (also called voxels) of the volume of the excited slice in a predetermined manner.

However, here the problem occurs that a highly complex equation system has to be solved. This follows directly from the known Bloch equation:

$$\frac{d\vec{M}}{dt} = \gamma \vec{M} \times \vec{B}_1 \quad (1)$$

where M is the magnetization, t is time, and $\vec{B}_1$ designates the deflection field. Usually, the formula also contains terms that describe the relaxation, which can be neglected since the duration of the excitation is very much shorter than time constants T1 and T2. References hereinafter to the Bloch equation are to be understood as referring to equation (1). The desired homogenous, or homogenous in particular regions, magnetization accordingly results as a time integral over the duration of the pulse sequence (one millisecond, or a number of milliseconds), or, in the time-discretized (use of incremental time steps) case, as a sum over all time steps. This desired magnetization is thus prespecified, while it has to be determined which combination of B1 fields and gradient fields, from which the feed parameters for the transmit channels can then be derived, results in this magnetization.

However, due to its vector nature and the discretization in space and time that is to be carried out, the Bloch equation decomposes into a multiplicity of equations that form an equation system. If it is taken into consideration that each transmit channel (for example 8) requires a complex-valued coefficient (i.e., amplitude and phase as feed parameters) for each time unit (conventionally several 100 during a 1 ms duration of the overall excitation pulse), with the use of the Bloch equation there results an equation system having several thousand variables. The desired magnetization (e.g. homogenous), or the desired magnetization distribution (e.g. homogenous in a particular region) in the selected slice is entered into this equation system.

Pulse calculation methods known for this purpose proceed from a small-angle approximation that enables a linearization of the resulting equation system; this means that the methods begin from small deflection angles. The inputs into the equation system are then real and imaginary parts of the desired magnetization; here the magnetization is permitted to amount to only a few percent (e.g. <10%) of the equilibrium magnetization, in order to make the small angle approximation permissible.

Apart from the fact that this solution approach does not permit large deflection angles, another problem that occurs cannot be taken into account. The application of gradient fields during RF radiation results in spatially selective excitation. Therefore, the overall introduced power loss, i.e. the SAR (specific absorption rate), increases, which can result in an exceeding of prespecified boundary values and danger to the patient. In addition, phenomena known as hotspots can occur in the individually excited regions, i.e. regions in which the SAR is locally particularly high. Finally, the taking into account of further quantities that limit the excitation pulses is not possible, or is possible only with difficulty, for example in the case of limited output power of the RF amplifier.

SUMMARY OF THE INVENTION

An object of the present invention is to provide an improved method with which ideal excitation pulses for achieving desired magnetizations can be determined even for large deflection angles, taking into account further (linear and non-linear) limitations, in particular SAR limitations.

This object is achieved by a method of the general type described above wherein, according to the invention, a feed sequence, determined for a number of time steps of the pulse sequence, is specified for gradient coils of the magnetic resonance apparatus, for the time-dependent selection of regions of a selected slice or of a selected volume, a non-linear equation system is solved to obtain feed parameters of the individual transmit channels of the transmit coil for each time step, with specification of a desired target magnetization, and taking into account the feed sequence. The non-linear equation system is based on discrete values for time and space variables and, in addition to the equations resulting from the Bloch equation, which are non-linear in their feed parameters, includes at least one additional equation that describes boundary conditions.

Thus, in the method according to the present invention first a feed sequence is specified for the gradient coils. In addition to the slice selection gradient, the other gradient coils are thus also supplied with current in accordance with the feed sequence, in order to select, in different time steps, different regions within the selected slice or within the selected volume. Non-contiguous slice regions or partial volumes are also conceivable here. Thus, magnetizations can be specified in arbitrary regions. The feed sequence is thus already discretized temporally and spatially. The spatial discretization is expressed as the partitioning of the selected slice into different voxels.

Methods for determining such a feed sequence for gradient coils are well-known in the prior art. In particular, three-dimensional k-space trajectories are often selected that essentially follow a spiral curve, and that proceed through an interval of locus frequencies in order finally to build up magnetization in selected regions. Accordingly, with the specification of the feed sequence it is known which regions are affected in which time step by the pulses of the RF transmit coil.

By means of this specification and the additional specification of the desired target magnetization, according to the present invention a non-linear equation system for feed parameters of the individual transmit channels of the transmit coil for each time step is now to be solved. The feed parameters are the already-mentioned complex-valued coefficients, which reproduce the amplitude and phase with which the feeding into the feed-in points allocated to the transmit channels takes place. The non-linear equation system is discretized in space and time, as described above, and includes, in addition to the equations resulting from the Bloch equation (1), which are non-linear in their feed parameters, at least one additional equation that describes boundary conditions. In the present context, boundary conditions are all additional conditions that can be imposed on the solution (also called "criteria"). Accordingly, it is proposed not only to solve the Bloch equation as an equation system in its non-linear form, but also to use the resulting possibilities in order to introduce further boundary conditions into the equation system in the form of additional equations.

Therefore, no linearization of the equation system takes place, as is the case in the prior art; rather, a solution method for non-linear equation systems is advantageously used, in particular a non-linear least square method, in order to approximately determine the feed parameters. This measure alone already exhibits a number of advantages in comparison with the prior art. Thus, it is now possible to calculate the RF pulses even for arbitrary magnetizations or deflection angles. Whereas, due to the linearization, in conventional methods only small-angle excitations could usefully be calculated, it is now also possible to treat large-angle excitations.

Furthermore, the non-linear approach enables the specification only of the magnitude of the desired target magnetization, which is sufficient for the magnetic resonance image recording process. With the use of a linearized equation system, this was not possible, because the magnitude formation is a non-linear process. Due to the fact that now the indication of the magnitude is sufficient, more degrees of freedom are now available for the achieving of additional goals, for example the minimization of patient exposure.

A further advantage is that many non-linear solution methods allow the limitation of the variables, which in the present case corresponds to a limitation of the maximum output power of the RF amplifier. Thus, the determination of the pulse sequence can be adapted to the available RF hardware. However, the greatest advantage of the non-linear approach is that additional, in particular also non-linear, equations can be added that can be immediately taken into account in the solution, i.e., simultaneously with the desired target magnetization.

In a preferred specific embodiment of the method according to the present invention, at least one equation whose feed parameters are non-linear and that describes the SAR exposure is used as an additional equation. The non-linear approach thus makes it possible in particular to incorporate the non-linear equations that describe the SAR exposure immediately into the solution of the equation system since, for example, boundary values for the SAR can enter immediately into the pulse calculation. In this way, exposure of patients to an impermissibly high SAR can be avoided. With the specification of a constant, i.e. maximally homogenous, target magnetization (one equation per voxel and time step), and simultaneously a very low target power loss (e.g. 0; supplies an additional equation for the overall power loss in each time step, or an equation, if summation takes place over all time steps), the approximate solution of the non-linear equation system supplies a pulse sequence that results in good to very good homogeneity of the magnetization, and simultaneous low overall power loss, i.e. low patient exposure.

There are essentially two possibilities for introducing equations that describe the SAR-relevant power loss. On the one hand, it can be provided that an equation indicating the power loss in the patient as a function of the vector-valued scatter variable, which is an immediate function of the feed parameters, and as a function of the scatter parameter matrix, is used as an additional equation. This connection of the power loss with the scatter parameter matrix is physically generally known, and can be expressed in an equation as:

$$PL \approx \sum_N a^+(I - S^+S)a, \qquad (2)$$

where PL represents the overall power loss, N stands for the time steps, a stands for the scatter parameters that correspond to the complex-valued coefficients, i.e. the feed parameters, of all channels for a time step, S designates the scatter parameter matrix and I designates the unit matrix, and "+" stands for "complexly conjugated and transposed." The SAR results, as is standard, from division by the corresponding weight.

The scatter parameter matrix can be determined by means of a three-dimensional electromagnetic simulation; a human model can be used, for example, as a basis, but it is advantageously also possible to measure the scatter parameter matrix. Here, all methods known from the prior art may be used. The use of an additional equation comprising the scatter parameter matrix thus has the advantage that this matrix can be measured, but has the disadvantage that only the overall power loss, or the power loss per time step, can be regarded, so that in this way hotspots cannot be localized.

Therefore, another variant of an additional equation that describes the SAR exposure is possible. In another specific embodiment of the present invention, it is provided that an equation indicating the power loss in the patient as a function of the electrical field distribution, which is a function of the feed parameters, and as a function of the conductivity distribution is used as an additional equation. This equation, resulting from the fundamental physical relations, can be notated as follows:

$$PL \approx \sum_{v=1}^{V} \sigma_v \sum_{n=1}^{N} \left| \sum_{ch}^{R} \vec{E}(v, t_n, ch) \right|^2, \quad (3)$$

PL again indicating the overall power loss, σ indicating the conductivity distribution, V, with associated continuous index v, indicating the voxels or the volume units, N indicating the number of time steps with continuous variable n, t indicating time, $\vec{E}$ indicating the electrical field distribution, R indicating the transmit channels, with continuous variable ch. This equation has the advantage that by using it, it is also possible to take into account the local SAR, in that instead of the overall equation the individual v summands are considered. It is therefore advantageously possible to regard additional equation (3) in spatially-resolved fashion. Therefore, using additional non-linear equations in the equation system, a specifiable number of the highest local SAR hotspots can be included in the pulse calculation, in order to keep the local SAR value below a limit, or below a particular ratio relative to the global SAR value. Thus, it can be provided that the locus-resolved additional equations describe the local SAR value. The computing expense can be further reduced here if the spatially-resolved additional equations are regarded so as to be limited to defined regions at which the highest local SAR values occur (hotspots). Here, 5-10 such regions can already be sufficient. Thus, for the first time the method according to the present invention makes it possible to act in a targeted manner towards prevention of the occurrence of such SAR hotspots.

While it can be provided according to the present invention that the tissue distribution is determined for example from previous image exposures of a patient, in particular magnetic resonance and/or computer tomography exposures, from which the conductivity distribution can then be determined because the frequency-dependent conductivities of various tissue types are known, a measurement method for the electrical field distribution is not known. However, for a given conductivity distribution in a patient, this can be determined particularly advantageously through a three-dimensional electromagnetic simulation. Here, for example, for the determination of the tissue distribution a human model may preferably be used that determines the tissue distribution in particular on the basis of input data about the patient. Thus, for example data about the patient taken from an electronic patient file, for example concerning the patient's sex, weight, height, age, etc., can be used to produce a tissue distribution of the human being in a human model. These data then form the basis for a three-dimensional electromagnetic simulation whose result is the electrical field distributions in the feeding of each individual transmit channel. In this way, it is possible also to use equation (3) as an additional equation in the method according to the present invention.

In addition to the indirect determination of the conductivity distribution from the tissue distribution from previous image exposures of a patient, it is likewise possible to determine the conductivity distribution directly using electrical impedance tomography. The determination of the conductivity distribution on the basis of conductivity atlases stored in tables is another alternative.

In general, the solution of the non-linear equation system using additional equations for the description of boundary conditions offers a series of further possibilities for the advantageous realization of the method. Thus, as already mentioned, it is possible to specify minimum and/or maximum values for the feed parameters that then correspond to limitations of the RF hardware, in particular of the RF amplifier.

In another advantageous specific embodiment of the method according to the present invention, it can also be provided that in order to adjust the solution, weighting factors can be used for the weighting of the equations of the equation system. In this way, the equations of the equation system can be allocated a value that indicates the importance with which this equation has to be fulfilled. This is particularly advantageous in order to adjust the determined solution, i.e. the determined feed parameters, between the partially contradictory goals (e.g., high homogeneity of the magnetization and low patient exposure), toward one goal or the other. For example, the equations resulting from the Bloch equation can be provided with one weighting factor, and the additional equation or equations can be provided with another weighting factor.

In order to check the adherence to the SAR boundary values, it can also be provided that after the determination of the feed parameters, the SAR exposure is determined from these parameters. Such an additional check may be advantageous in the interest of patient safety. If it is found that the SAR exposure is for example still too high, weighting factors can be changed, or for example the additional equations can be formulated using other boundary values. Thus, in principle it is also conceivable using the method according to the present invention to carry out an iterative optimization process in which several passes take place through the method according to the present invention in order finally to reach an ideal compromise between the lowest possible patient exposure and maximum homogeneity.

Here it is again to be noted that using the method according to the present invention it is also possible in an improved manner to selectively excite only particular regions of the selected slice or the selected volume, using a target magnetization.

In particular, as presented above, it is indeed also possible that not necessarily a slice will be regarded, but rather an arbitrary volume. In a specific embodiment of the method according to the present invention, slice selection gradient is not used at all; this means that the feed sequence feeds only the gradient coils not used for slice selection. For example, therefore, only the gradient coils in the x and y direction are fed, so that a volume excitation takes place that is extended in the z direction.

The determined feed parameters are then finally used in order to feed—synchronously with the feed sequence of the gradient coils—the various transmit channels of the RF transmit coil, and thus to obtain the corresponding magnetization.

A magnetic resonance apparatus according to the present invention that uses the method according to the present invention can for example comprise an input unit and a feed unit. An operator can input a desired magnetization via the input unit, whereupon the feed unit, which is designed to execute the method according to the present invention, automatically determines the feed parameters for the RF transmit coils in accordance with the method according to the present invention, given the prespecified feed sequence for the gradient coils, and feeds these coils correspondingly.

The method according to the present invention can also be used for RF transmit coils having a low number of channels. In particular, embodiments have been proposed in which the signal supplied by the RF amplifier can be divided among two or more modulation units whose modulation parameters then correspond to the feed parameters for the present method. For these cases as well, the method can advantageously be used.

DESCRIPTION OF THE PREFERRED EMBODIMENTS

Figure 1:
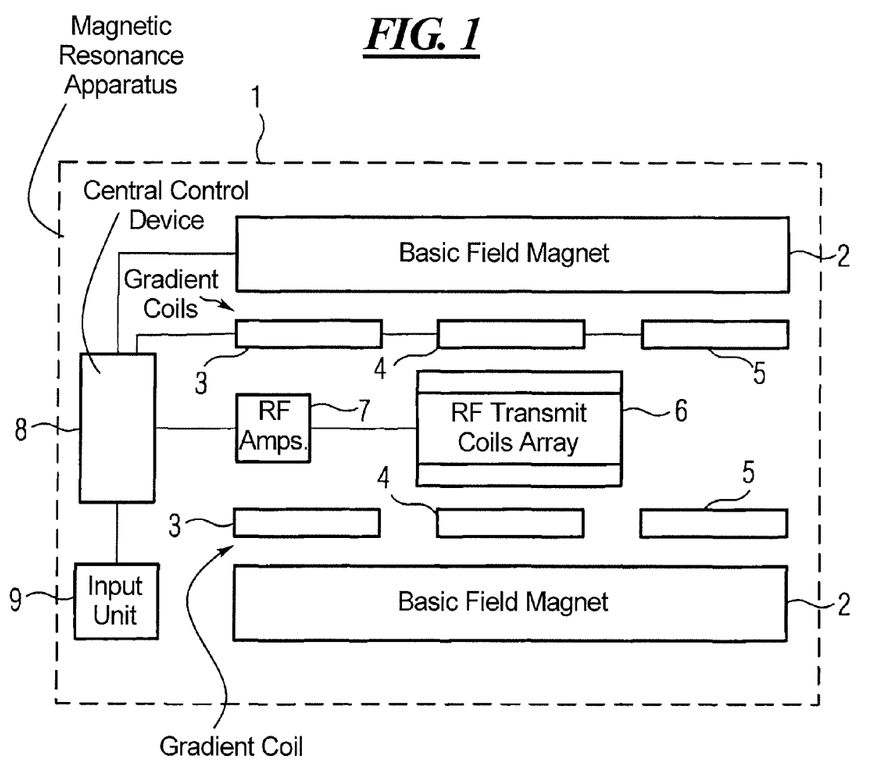
FIG. 1 schematically illustrates a magnetic resonance apparatus according to the present invention.

FIG. 1 shows a magnetic resonance apparatus 1 with which the method according to the present invention can be realized, in a schematic representation. Magnetic resonance apparatus 1 has a basic field magnet 2 that produces a static magnetic field having a strength greater than or equal to 3 Tesla. In addition, three gradient coils 3, 4, 5 are provided, gradient coil 3 being allocated to the z direction, in which the excitation pulse sequence thus forms the slice selection gradient. Gradient coils 4 and 5 produce gradients in the x and y directions respectively. In addition, an array 6 of RF transmit coils is provided; in this case, birdcage coils, which can also be used as receive coils, can be used. The array has eight transmit channels via which a pulse sequence, determined by feed parameters, is radiated in order to homogenously deflect the nuclear spins of the patient being examined out of the equilibrium magnetization. The RF fields required for this are produced by a number of RF amplifiers 7. Here, an amplifier 7 feeds a transmit antenna of array 6. Alternatively, one amplifier 7 can feed a number of transmit antennas, in which case a modulator and phase shifter are to be allocated to each transmit antenna in order to enable a supply of current that is independent in amplitude and phase. The method according to the present invention can of course also be used in cases in which only one transmit coil is present.

In addition, for magnetic resonance apparatus 1 a central control device 8 is provided via which the various components of magnetic resonance apparatus 1, in particular coils 3-6, can be fed. Control device 8 is designed for the execution of the method according to the present invention, and thus calculates, given specification of a feed sequence for the gradient coils and a desired target magnetization, feed parameters for a pulse sequence, and then correspondingly feeds gradient coils 3, 4, 5, and in particular the transmit channels of the RF transmit coils of array 6. In addition, an input unit 9 is allocated to feed device 8, via which unit a user can input corresponding parameters for magnetic resonance apparatus 1, in particular input data for the method according to the present invention.

Figure 2:
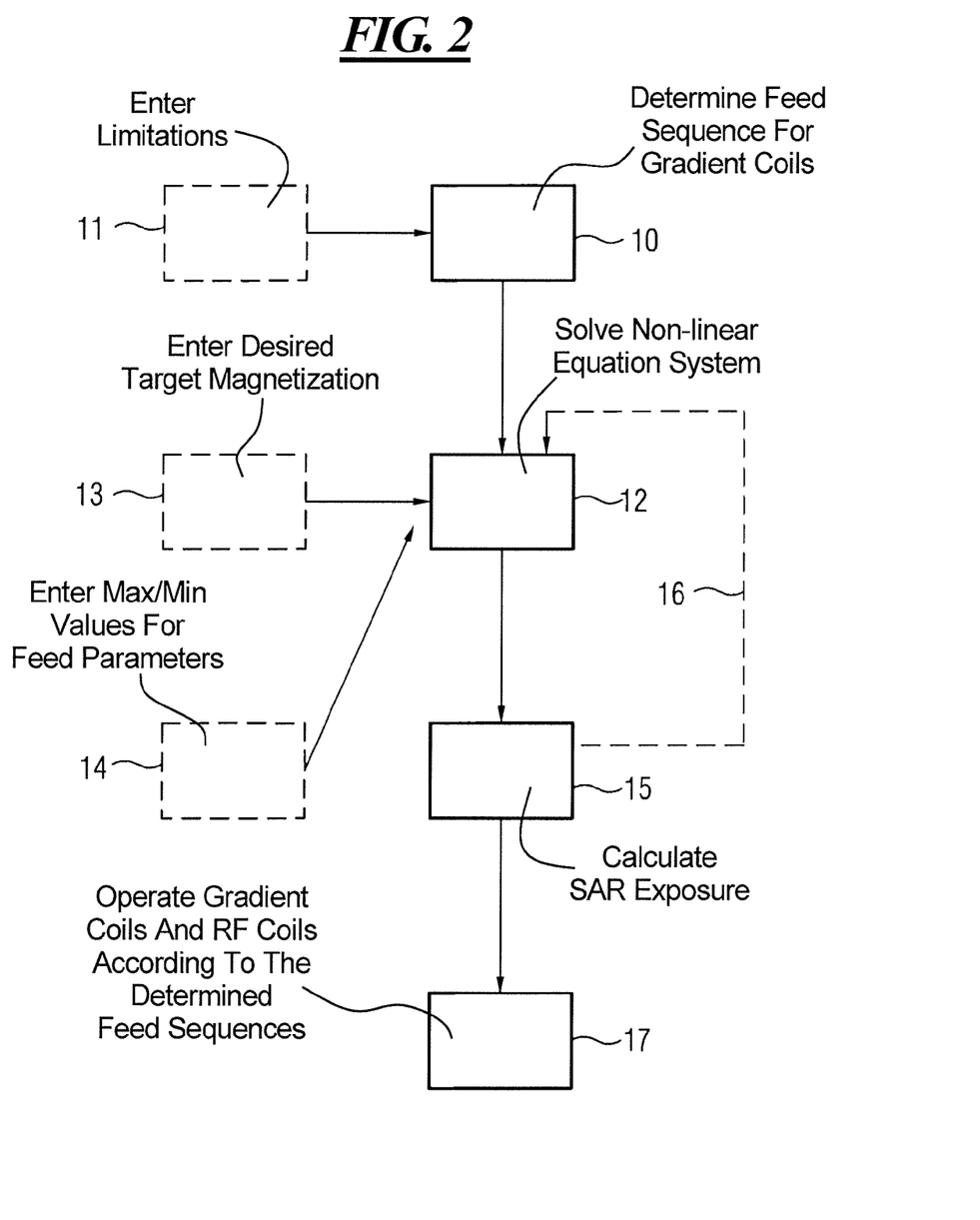
FIG. 2 shows a sequence plan of the method according to the present invention.

FIG. 2 shows a sequence plan of the method according to the present invention.

Figure 3:
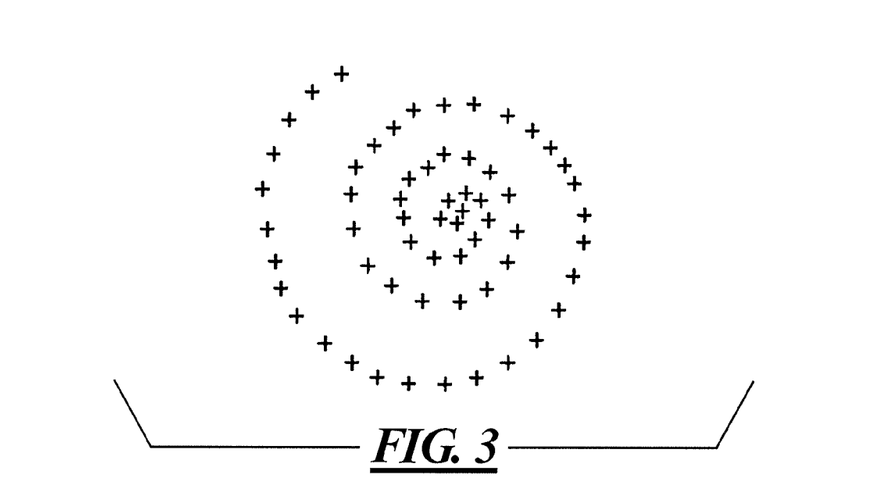
FIG. 3 shows the k-space trajectory of a feed sequence for gradient coils.

In a step 10, first a feed sequence that is to be specified for the gradient coils is determined or sought. Limitations of the allocated hardware and of gradient coils 3, 4, 5 themselves are entered here as quantities to be taken into account; box 11. While the slice selection gradient, produced by gradient coil 3, can be active continuously during the pulse sequence, gradient coils 4 and 5 are also switched (activated) in individual time steps during the pulse sequence in order to select particular regions of the selected slice. A k-space trajectory, an example of which is shown in FIG. 3, has turned out to be particularly suitable as a feed sequence. The k-space trajectory runs in a spiral shape, and thus acquires a particular interval of locus frequencies. Each individual point shown in FIG. 3 corresponds to gradient coil parameters for a time step.

Once the feed sequence is known for gradient coils 3, 4, 5, in a step 12 a non-linear equation system is solved using a non-linear least square solution method. The equation system is composed of the time-and-space-discretized non-linear equations derived from the Bloch equation (1), the feed parameters entering into the equations via the corresponding $B_1$ values, as well as additional equations. The additional equations, of which there may be only one, describe boundary conditions, in the present case the SAR exposure, and are themselves non-linear in this exemplary embodiment. In the present case, two equations that describe the SAR exposure are conceivable, namely equations (2) and (3), which are described in more detail below. The additional equation or equations are formed using a maximum power loss (and thus maximum SAR), so that as boundary conditions SAR boundary values enter into the equation system through the additional equations in an elegant manner, so that they can be taken into account immediately in the solution of the system, and no additional, expensive computing processes need take place.

In addition to the feed sequence, as an input quantity the magnitude of the desired target magnetization is first also required for all voxels or volume units; box 13. The desired target magnetization is the integral over the Bloch equation (1). As target magnetization, a target magnetization can be provided that is homogenous in the overall selected slice; however, an arbitrary magnetization distribution, for example a magnetization only in particular regions, can also be provided.

In addition, as input quantities for step 12, minimum and maximum values can be specified for feed parameters; box 14. With the use of the least square solution method, it is possible to limit the size of the feed parameters. These minimum and/or maximum values are determined by the hardware properties in particular of RF amplifier 7.

For the selection of the additional equation (s), there are essentially two possibilities, namely equations (2) and (3). Both possibilities have their advantages and disadvantages, and are correspondingly selected according to the needs of the situation.

With equation (2), via the scatter parameter matrix, the feed parameters enter directly into in the equation via the scatter parameters. In addition, the scatter parameter matrix can advantageously be measured. It is of course also possible to determine the scatter parameter matrix through a corresponding three-dimensional electromagnetic simulation, for example using a human model. However, equation (2) offers only one access to the overall power loss, or to the overall power loss for a time step. Therefore, no local hotspots can be excluded in a targeted manner.

The situation is different if equation (3) is used. Equation (3) can be broken down into individual equations for each voxel or each partial volume, so that SAR limitations can also be locally specified. However, the disadvantage is that heretofore no access using measurement technology is known to the electrical field distribution containing the feed parameters, so that this distribution has to be determined via a simulation. For this purpose, the tissue distribution of the patient must be known. However this can be realized by using an adaptable human model, which can be adapted for example on the basis of patient parameters such as height, weight, age, sex, etc. It is then possible, using a three-dimensional electromagnetic simulation, to determine the electrical field distribution. The conductivity distribution, which also enters into equation (3), can be determined indirectly in the method according to the present invention from the tissue distribution, from previous image exposures, in particular magnetic resonance or computed tomography exposures, or directly from the impedance tomography, or on the basis of conductivity atlases stored in tables.

Once the equation system in step 12 has been solved, and if approximate values are present for the feed parameters, in an optional step 15 the SAR exposure, in particular the local SAR exposure, can be calculated therefrom. In this way, it can be checked again whether all boundary values have been observed, i.e. whether an optimal pulse sequence is present. If this is not the case, it can be provided, as indicated by arrow 16, that for example the equations of the equation system, or their weighting factors, are correspondingly modified in order to carry out a new calculation. Thus, an optimization process is conceivable in which steps 12 and 14 are repeated several times until an optimization criterion has been reached.

In the method according to FIG. 2, the equations of the non-linear equation system are additionally provided with weighting factors that reproduce a corresponding valuation. By setting these weighting factors, for example one weighting factor for the equations resulting from the Bloch equation and another weighting factor for the additional equations, it is possible practically to set the specifications toward which the solution should be oriented given conflicting interests, for example if the requirements of homogeneity and of low SAR exposure are in conflict.

Finally, in step 17 control device 8 feeds gradient coils 3, 4, 5 and the channels of RF transmit coil 6 according to the feed sequence and the determined feed parameters, so that an optimal pulse sequence results with which an improvement is achieved both of the homogeneity and of the SAR exposure.

Figure 4:
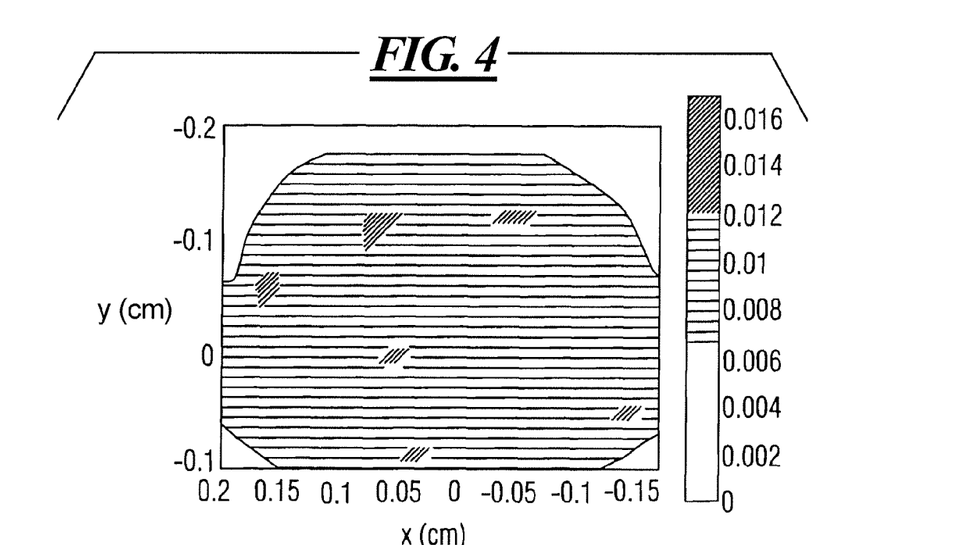
FIG. 4 shows a magnetization distribution achieved using the method according to the present invention.
Figure 5:
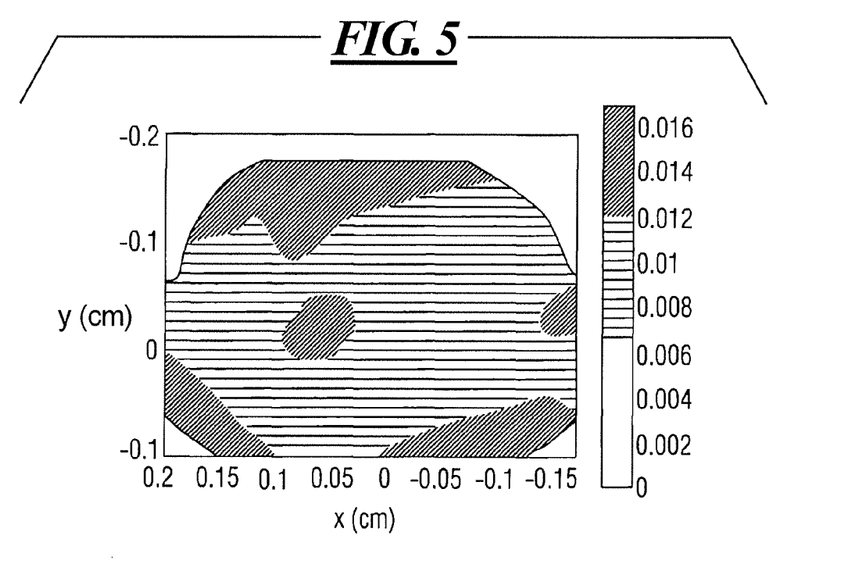
FIG. 5 shows a magnetization distribution according to the prior art, achieved using a mode 1 excitation.

This is presented in more detail in an example in FIGS. 4 and 5. In this example, a body coil is considered having eight transmit channels, and, given a small angle excitation (deflection (flip) angle 0.57°) a homogenous magnetization of 1% of the equilibrium magnetization is to be achieved. FIG. 4 shows the results for the magnetization distribution using the method according to the present invention, in which hatched areas signify a deviation, the strength of the hatching indicating the strength of the deviation. FIG. 5 shows the magnetization distribution that would be achieved in the same patient given a mode 1 excitation. It will be seen that the deviations are significantly stronger. In fact, using the method according to the present invention the homogeneity was improved by a factor of 5 relative to the mode 1 excitation (the standard deviation of the magnetization was regarded relative to the mean value of the magnetization in a cross-sectional surface of the thorax, without the arms). Here, the overall power loss is only 1.5 times that of a mode 1 excitation, which results in the same mean magnetization for the same pulse duration.

The method according to the present invention can also be used for large-angle excitations, for example a deflection angle of 48.6°. Corresponding trials for a head coil having eight transmit channels yielded the result that with the use of the method according to the present invention the homogeneity can be improved by almost a factor of 3, the overall power loss with the method according to the present invention being only 75% of a mode 1 excitation.

Thus, using the method according to the present invention extreme improvements can be achieved while observing SAR boundary values.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a pulse sequence for feeding a radio-frequency (RF) radiating coil, having at least one transmit channel associated therewith, of a magnetic resonance apparatus that also comprises gradient coils, said method comprising the steps of:
    in a processor, specifying a feed sequence, determined for a plurality of time steps of said pulse sequence, for operating said gradient coils for time-dependent selection of regions of at least a selected slice of a subject in a magnetic resonance examination of the subject;
    in said processor, automatically solving a non-linear equation system to obtain drive parameters for each transmit channel of said RF radiating coil for each of said time steps, with specification of a desired target magnetization in the subject, and dependent on said feed sequence specified for said gradient coils; and
    in said processor, employing, as said non-linear equation system, a non-linear equation system having discrete space and time variables that, in addition to equations resulting from the Bloch equation, which are non-linear with regard to feed parameters thereof, also includes at least one additional equation describing boundary conditions for said magnetic resonance examination.

2. A method as claimed in claim 1 comprising, in said processor, employing, as said additional equation, at least one equation describing an SAR exposure for said subject, which is non-linear with regard to drive parameters thereof.

3. A method as claimed in claim 2 comprising, in said processor, employing, as said at least one equation, an equation that indicates a power loss in the patient as a function of a vectorized scatter variable, said vectorized scatter variable being a direct function of said feed parameters of said at least one equation, and as a function of a scatter parameter matrix.

4. A method as claimed in claim 3 comprising determining said scatter parameter matrix in said processor by three-dimensional electromagnetic stimulation of the subject.

5. A method as claimed in claim 3 comprising measuring said scatter parameter matrix with regard to said subject.

6. A method as claimed in claim 2 comprising employing, as said equation indicating power loss in the subject, an equation that is a function of an electrical field distribution in the subject that is a function of said feed parameters of said equation indicating power loss, and that is a function of a conductivity distribution in the patient.

7. A method as claimed in claim 6 comprising determining said conductivity distribution from a tissue distribution from a previous image exposure of the subject, selected from the group consisting of magnetic resonance exposures and computed tomography exposures.

8. A method as claimed in claim 6 comprising, in said processor, automatically determining said field distribution from a predetermined conductivity distribution in the subject resulting from a three-dimensional electromagnetic stimulation of the subject.

9. A method as claimed in claim 8 comprising using a computerized human model in said processor to determine said tissue distribution, said model representing tissue distribution dependent on personal and physiological data describing the subject entered into the processor.

10. A method as claimed in claim 6 comprising determining said conductivity distribution by electrical impedance tomography implemented on the subject.

11. A method as claimed in claim 6 comprising employing a spatially-resolved equation as said additional equation.

12. A method as claimed in claim 11 comprising employing, as said spatially-resolved equation, an equation describing a localized SAR value of the subject.

13. A method as claimed in claim 1 comprising solving said equation system using a non-linear least squares method.

14. A method as claimed in claim 1 comprising specifying, in said processor, values selected from the group consisting of maximum values and minimum values for said feed parameters.

15. A method as claimed in claim 1 comprising, in said processor, automatically determining weighting factors that respectively weight the equations of said equation system, when solving said equations of said equation system.

16. A method as claimed in claim 1 comprising employing SAR boundary values for solving said equation system in said processor, and, after solving said equation system in said processor, implementing an SAR exposure with said magnetic resonance apparatus, using the feed parameters obtained by solving said equation system, to confirm correct observance of said SAR boundary values in said SAR exposure.

17. A method as claimed in claim 1 wherein said gradient coils include gradient coils not used for said slice selection, and comprising specifying said sequence for feeding said gradient coils using only said gradient coils that are not used for slice selection.

18. A magnetic resonance apparatus comprising:
a magnetic resonance data acquisition unit comprising a radio-frequency (RF) radiating coil, having at least one transmit channel associated therewith, and gradient coils;
a processor configured to determine a pulse sequence for feeding said RF radiating coil;
said processor being configured to specify a feed sequence for a plurality of time steps of said pulse sequence, for operating said gradient coils for time-dependent selection of regions of at least a selected slice of a subject in a magnetic resonance examination of the subject;
said processor being configured to automatically solve a non-linear equation system for obtaining drive parameters for each transmit channel of said RF radiating coil for each of said time steps, with specification of a desired target magnetization in the subject, and dependent on said feed sequence specified for said gradient coils;
said processor being configured to employ, as said non-linear equation system, a non-linear equation system having discrete space and time variables that, in addition to equations resulting from the Bloch equation, which are non-linear with regard to feed parameters thereof, also includes at least one additional equation describing boundary conditions for said magnetic resonance examination; and
said processor emitting said drive parameters for each transmit channel of said RF radiating coil at an output of the processor in a form for operating said RF radiating coil.

* * * * *